United States Patent
Brown, III et al.

(10) Patent No.: US 8,812,085 B2
(45) Date of Patent: Aug. 19, 2014

(54) SYSTEM AND METHOD FOR MEASURING THE RATIO OF FORWARD-PROPAGATING TO BACK-PROPAGATING SECOND HARMONIC-GENERATION SIGNAL, AND APPLICATIONS THEREOF

(75) Inventors: Edward Brown, III, Honeoye Falls, NY (US); Xiaoxing Han, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/696,150

(22) PCT Filed: May 3, 2011

(86) PCT No.: PCT/US2011/034921
§ 371 (c)(1),
(2), (4) Date: Nov. 5, 2012

(87) PCT Pub. No.: WO2011/140030
PCT Pub. Date: Nov. 10, 2011

(65) Prior Publication Data
US 2013/0057873 A1    Mar. 7, 2013

Related U.S. Application Data

(60) Provisional application No. 61/330,619, filed on May 3, 2010.

(51) Int. Cl.
*A61B 6/00*  (2006.01)

(52) U.S. Cl.
USPC ............... 600/473; 600/476; 382/128

(58) Field of Classification Search
USPC ................ 600/407–480; 382/128–132
See application file for complete search history.

(56) References Cited

U.S. PATENT DOCUMENTS

2005/0258375 A1* 11/2005 Mertz et al. ............... 250/458.1
2010/0031748 A1*  2/2010 Simpson et al. ............... 73/579

OTHER PUBLICATIONS

Theodossis A. Theodossiou et al.; Second Harmonic Generation Confocal Microscopy of Collagen Type I from Rat Tendon Cryosections; Biophysical Journal vol. 91 Dec. 2006 4665-4677.
PCT International Search Report and Written Opinion, KIPO, Nov. 21, 2012.

* cited by examiner

*Primary Examiner* — Sanjay Cattungal
(74) *Attorney, Agent, or Firm* — William Greener; Bond, Schoeneck & King, PLLC

(57) ABSTRACT

A method and system that enable the measurement of a second-harmonic-generation-forward/backward (SHG F/B) ratio from an object by performing only a single image scan using via epi-imaging using an epi-detection technique. Two simultaneous SGH images (a forward propagating SHG "F" image and a back propagating SHG "B" image) are generated during the single image scan. A pinhole mirror can be used to separate the F-SHG and the B-SHG, which are detected by separate detectors.

14 Claims, 3 Drawing Sheets

(a) (b)

SYSTEM AND METHOD FOR MEASURING THE RATIO OF FORWARD-PROPAGATING TO BACK-PROPAGATING SECOND HARMONIC-GENERATION SIGNAL, AND APPLICATIONS THEREOF

US GOVERNMENT SPONSORSHIP

The invention was made with government support under Department of Defense BCRP Pre-doctoral Traineeship Award W81XWH-08-1-0323; Department of Defense BCRP Era of Hope Scholar Research Award W81XWH-09-1-0405; and NIH Director's New Innovator Award 1DP2OD006501-01. The government has certain rights in the invention.

REFERENCE TO RELATED APPLICATIONS

This application claims priority to U.S. Provisional Application No. 61/330,619 filed on May 3, 2010, the subject matter of which is hereby incorporated by reference in its entirety.

FIELD OF THE INVENTION

The present invention relates generally to the field of non-linear optics, more particularly, to an optical system and method for measuring the ratio of forward-propagating ("F") to back-propagating ("B") second harmonic-generation ("SHG") signal, and applications thereof and, most particularly, to said system, methods, and applications using epi-detection (i.e., only a single objective lens).

BACKGROUND

The measurement of the ratio of the forward-propagating ("F") to backward propagating ("B") SHG signal (the "F/B ratio") has reportedly been used to study collagen fiber ordering in various tissue samples. The F/B ratio revealed the length scale of ordering in the fibers, and in the case of osteogenesis imperfecta and ovarian cancer, was able to be used to discriminate pathological tissue from healthy tissue. This suggests that this technique might serve as a diagnostic tool for these diseases and possibly others in the future.

Previously reported SHG F/B ratio measurements were made in vitro, because a second objective lens was needed to collect forward propagating SHG signal and thus the tissue sample had to be dissected from the subject and sectioned to allow signal to reach the second detection lens. For clinical applications, as well as basic science applications in the in vivo setting, these requirements are problematic.

In Han et al., *Measurement of the ratio of forward-propagating to back propagating second harmonic signal using a single objective*, Optics Express, 2010. 18(10): p. 10538-10550, the instant [means 'current' in patentees] inventors reported on a SHG confocal imaging method that could produce F/B ratio measurements without a second lens (to collect the "F" SHG light) on the opposite side of the sample. The method involved taking SHG images over the same region of interest repeatedly through a series of confocal pinholes of different sizes. It allowed the successful measurement of rat tail collagen [not necessary for 'this' application] SHG F/B ratio in vivo, i.e., while the collagen fibers were still embedded in the tail. To the inventors' knowledge, this variable pinhole method was the first available imaging technique that allowed one to measure the SHG F/B ratio on intact tissue samples without sectioning, using just an epi-detection objective lens.

In the aforementioned variable pinhole method, five SHG images were taken over the same region of interest, which is a time consuming process. As a consequence, the sample must be kept stationary during the whole imaging process to avoid SHG intensity variation due to the movement of the sample. During in vivo applications, applications on extremely thick and soft tissues such as, but not limited to, tissue freshly removed from a subject during surgery, and in endoscopic use applications, for example, this can be problematic.

In view of the foregoing discussion of the shortcomings and problems associated with measuring the SHG F/B ratio on intact tissue samples without sectioning using just an epi-detection objective lens, such as but not limited to sample motion, the inventors have recognized the benefits and advantages of apparatus and methods that overcome such shortcomings and solve said problems.

In breast conservation surgery (BCS) the surgeon attempts to remove the primary breast tumor, plus a sufficient margin such that no tumor cells remain in the patient, while leaving as much of the breast untouched as possible. The surgeon can often take advantage of optical and tactile cues while performing the surgery, as well as radiographic imaging of the excised tissue, to deduce whether sufficient tissue has been removed to ensure that margins are clear, which is usually defined as no tumor cells within ~2 mm of the excised tissue surface. This is supported by subsequent pathology investigation, in which the excised tissue is thinly sliced, stained, and coarsely subsampled at high resolution by a pathologist, who determines the location of tumor cells relative to the surgical margin in those slides that are sampled. This assessment by the pathologist is especially important in tumors such as DCIS in which optical, tactile, and radiographic cues are minimal. Unfortunately, the pathologist is not able to look, at high magnification, at every cubic micron of excised tissue within 2 mm of the excised surface, is therefore forced to perform a subsampling, and hence can miss aberrant tissue, contributing to the number of patients whose tumors recur in spite of reportedly good margins. This negatively impacts patient outcomes. Furthermore, full assessment takes significantly more time than the duration of the surgical procedure, and patients must therefore return to the hospital for second and third surgeries when the conclusion is reached that their samples had poor margins. This negatively impacts patient quality of life.

In view thereof, it would be advantageous to develop a method for rapid margin assessment in the operating room, particularly applicable to intact (i.e. unsliced) tissue section typically removed during breast conservation surgery.

SUMMARY OF THE INVENTION

An embodiment of the invention is a method for measuring a second-harmonic-generation-forward/backward (SHG F/B) ratio from an object by performing only a single image scan. The method involves the steps of irradiating an object in a manner to generate a second harmonic generation (SHG) emission in an object plane from the object; imaging the SHG object plane via epi-imaging onto a confocal image plane; separating a direct backward-propagating SGH ("B") portion and a backscattered forward-propagating SHG ("F") portion of the SHG emission; detecting the F portion with a first detector and the B portion with a second detector; and measuring the SHG F/B ratio using only a single image scan. According to various non-limiting aspects:

the step of separating the B portion and the F portion further comprises propagating the F portion through a clear aperture in the confocal image plane to the first detector and reflecting the B portion from the confocal image plane to the second detector;

the method further comprising disposing a pinhole minor having the clear aperture and a reflective surface in the confocal image plane, wherein the clear aperture has a minimum radius equal to or greater than about 10 microns (note that the pinhole radius is greater than w, where w is the $e^{-2}$ Gaussian spot size of the direct backward propagating SHG in the confocal plane. The upper limit of the pinhole size can vary as a function, at least in part, of the optical system magnification);

the method further comprising disposing a pinhole minor having the clear aperture and a reflective surface in the confocal image plane, wherein the total SHG emission distribution on the object plane is expressed as $$I_{SHG}(r) = B\exp\left[-2\left(\frac{r}{\omega}\right)^2\right] + FC,$$

where, again, $\omega$ is the $e^{-2}$ Gaussian spot size of the direct backward propagating SHG, F and B are absolute intensities of forward and backward propagating SHG signals, C relates the initial forward propagating signal intensity to the average intensity of the uniform distribution of SHG light that reaches the object plane and is a function of scattering and absorption properties of the underlying tissue, and has a value between $10^{-4}$ and $10^{-3}$.

An embodiment of the invention is an optical system that can be used to measure a SHG F/B ratio from a sample in a single image scan using only a single object imaging lens component (referred to herein as "epi-imaging" and akin to the known optical technique of 'epi-detection'). The system includes a beam scanning component; an object plane imaging component optically coupled to the beam scanning component, wherein the object plane imaging component is an epi-imaging system; an imaging component disposed in an optical path of the system to provide a conjugate image of the object plane in an image plane; an image discriminating component disposed in the image plane; a first detector disposed in a first optical path from the image discriminating component; and a second detector disposed in a second optical path from the image discriminating component. According to various non-limiting aspects:

the object imaging component is a microscope;

the imaging component is one or more imaging lens elements;

the image discriminating component is a pinhole minor;

the first detector is disposed adjacent one side of the pinhole minor and the second detector is disposed adjacent an opposite side of the pinhole mirror;

the pinhole mirror has a central clear aperture and a reflective surface outside of the central clear aperture;

the central clear aperture has an anti-reflection coating;

the pinhole mirror has a central clear aperture having a minimum radius equal to or greater than about 10 microns (note that the pinhole radius is greater than ω, where ω is the $e^{-2}$ Gaussian spot size of the direct backward propagating SHG in the confocal plane. The upper limit of the pinhole size can vary as a function, at least in part, of the optical system magnification);

the optical system further comprising a spectral filter disposed in front of the first detector;

the optical system further comprising a spectral filter disposed in front of the second detector.

DETAILED DESCRIPTION OF EXEMPLARY EMBODIMENTS

Figure 1:
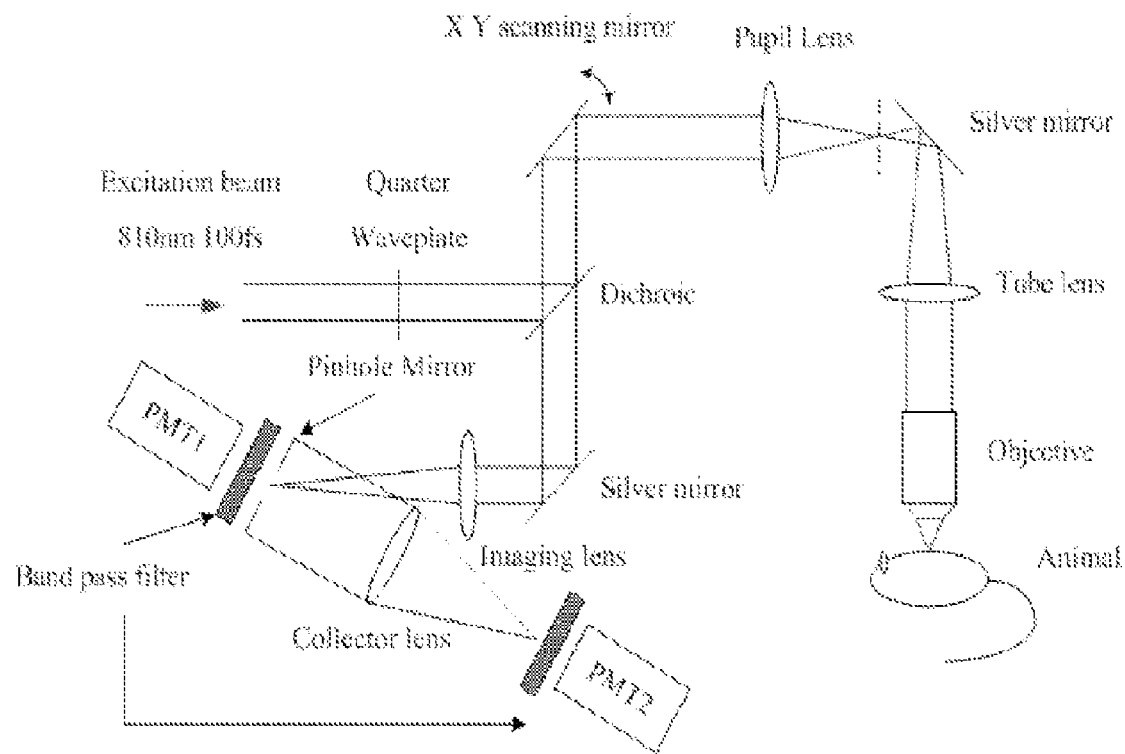
FIG. 1 schematically shows an experimental setup for the embodied pinhole minor imaging method, according to an illustrative aspect of the invention.

A non-limiting, illustrative, exemplary embodiment of an optical system 100 [refers to components in the drawings-required in a patent application] that can be used to measure a SHG FB ratio from an object sample 101 in a single image scan is schematically illustrated in FIG. 1. In operation, SHG-producing signal was generated by a Spectra Physics MaiTai Ti:Sapphire laser 802 providing 100 femtosecond (fs) pulses at 80 megahertz (MHz) at a wavelength λ equal to 810 nanometers (nm); i.e., excitation beam 804 (solid line beam). A quarter wave plate (Thorlabs WPMQ05M-830) 803 was used to convert the linearly polarized excitation beam to circularly polarized. The beam 804 was then directed into an Olympus Fluoview F300 scanhead connected to an Olympus BX61WI upright microscope by a dichroic minor (Chroma 670 DCSX) 809. The focusing objective 811 is an Olympus UMPLFL20XW water immersion lenses (20×, 0.5 NA). These components are represented within the dotted box 807. The SHG beam 805 (dotted line beam) was separated from the excitation beam and directed out of the scanhead by the dichroic minor 809, and then imaged onto a pinhole minor 813 with an imaging lens 814. SHG 805-1 that passed through the pinhole minor was filtered by a 405 nm bandpass filter (Chroma HQ405/30m-2p) 415-1 and detected by a photomultiplier tube (HC125-02, Hamamatsu) PMT1. SHG signal 805-2 reflected from the pinhole mirror was focused through a second 405 nm filter 415-2 and subsequently detected by a second photomultiplier tube PMT2.

Those skilled in the art will understand that the system components named herein above are merely exemplary and that different functional components may instead be used; for example, a suitable SHG excitation source may advantageously emit pulses in the 10-1000 fs range; the objective lens may advantageously have a numerical aperture (NA) less than, equal to, or greater than 0.1; a filter may advantageously have a different bandpass depending on the selected sample and SHG emission. Typically, if the SHG-excitation wavelength is $\lambda_x$, then the filter bandpass may advantageously be centered at $\lambda_x/2$, with the understanding that SHG emission is to be transmitted and autofluorescence and other unwanted wavelengths filtered out.

In an illustrative aspect, the pinhole minor 813 is a simple aluminum reflecting mirror having a small clear aperture ("pinhole") of appropriate size at the center. The pinhole mirror is used here to separate the direct backward propagating SHG 805-1 (FIG. 1) from the backscattered forward propagating SHG 805-2 (FIG. 1). The illustrative mirror was made as follows: a 1.05 mm thick glass substrate was anti-reflection (AR) coated to minimize reflections at 405 nm (Accucoat Inc, Rochester, N.Y.); a 2 mm diameter droplet of oil was placed on the surface; and aluminum was deposited on the substrate surface by vacuum evaporation using a high vacuum evaporator (Ladd Research Industries, Williston, Vt.). The oil droplet was washed off, resulting in a 2 mm "pinhole," with an AR coating on the glass within the pinhole region. We did not determine the effect of the AR coating on the performance of the apparatus. Those skilled in the art will appreciate that other techniques can be used to create a "pinhole mirror" and that other pinhole mirror designs may be suitable for carrying out the invention (e.g., reflective surface with a central opening of appropriate size). Pinhole size will be discussed in greater detail below.

When the excitation illumination 804 is focused at the surface of an object of interest and the object plane is imaged onto a confocal plane, the spatial distribution of SHG signal on the confocal plane will consist of a sharp central peak due to the backward propagating SHG (405-1) plus a diffuse signal due to the forward propagating and subsequently back-scattered SHG (405-2). The image of the direct backward propagating SHG signal can be modeled as a Gaussian spot, while the forward propagating SHG that subsequently back-scatters is modeled as a uniform distribution. Thus the total SHG signal intensity distribution on the object plane can be expressed as $$I_{SHG}(r) = B\exp\left[-2\left(\frac{r}{\omega}\right)^2\right] + FC, \quad (1)$$

where $\omega$ is the $e^{-2}$ Gaussian spot size of the direct backward propagating SHG, and F and B are the absolute intensities of the forward and backward propagating SHG signals. The parameter C relates the initial forward propagating signal intensity to the average intensity of the uniform distribution of SHG light that reaches the object plane. It is a function of scattering and absorption properties of the underlying tissue and has typical values ranging between $10^{-4}$ and $10^{-3}$.

The direct backward propagating SHG decays very quickly from the peak value as the distance from the laser axis increases. For example when $r=3\omega$, the direct backward propagating SHG decays to $\exp(-18)=1.5\times10^{-8}$ of its peak value. Consequently, for F/B ~1 and typical C values, the intensity of the back-scattered forward propagating SHG signal is about $10^{-4}$-$10^{-3}$ of the peak intensity of the direct backward propagating SHG signal, and the direct backward propagating SHG at $r\geq 3\omega$ will be significantly less intense than the forward propagating SHG signal that subsequently backscatters. Therefore, for a pinhole mirror located in the confocal plane, if the radius of the pinhole is ~3$\omega$ or greater (i.e., ~$\geq$30 µm), we may confidently assume that there is no direct backward propagating SHG signal outside the pinhole. As such, the SHG signal inside the pinhole area can be expressed by $$I_{pinhole} = \int_0^{2\pi} d\theta \int_0^{n\omega} \left\{B\exp\left[-2\left(\frac{r}{\omega}\right)^2\right] + FC\right\}rdr. \quad (2)$$

This signal will go through the pinhole and can be detected by PMT-1 (FIG. 1). The SHG signal outside of the pinhole can be expressed by $$I_{Mirror} = FC(\pi R^2 - \pi n^2 \omega^2). \quad (3)$$

Here, $n \geq 3$ and represents the size of the pinhole with respect to $\omega$, which is the SHG Gaussian spot size in the pinhole mirror plane. R is the radius of the whole mirror (if it is round), or that part of the mirror that is imaged onto the round photocathode of PMT-2 (FIG. 1). This signal will miss the pinhole and be reflected by the mirror. The collector lens will then collect the signal from the mirror and this signal will be detected by PMT-2.

Considering the transmission and reflection coefficients of the pinhole and the mirror, the SHG intensity detected by PMT-1 and PMT-2 can be compared as follows:

$$\frac{P}{M} = \frac{T\%}{R\%} \cdot \alpha \cdot \frac{\frac{B}{2}\pi\omega^2[1-\exp(-2n^2)] + FC\pi n^2\omega^2}{FC(\pi R^2 - \pi n^2\omega^2)} \quad (4)$$
$$= A \cdot \alpha \cdot \left[\frac{B}{F} \cdot \frac{1}{2C}(1-\exp(-2n^2)) + n^2\right]\frac{\omega^2}{R^2 - n^2\omega^2}.$$

Figure 2:
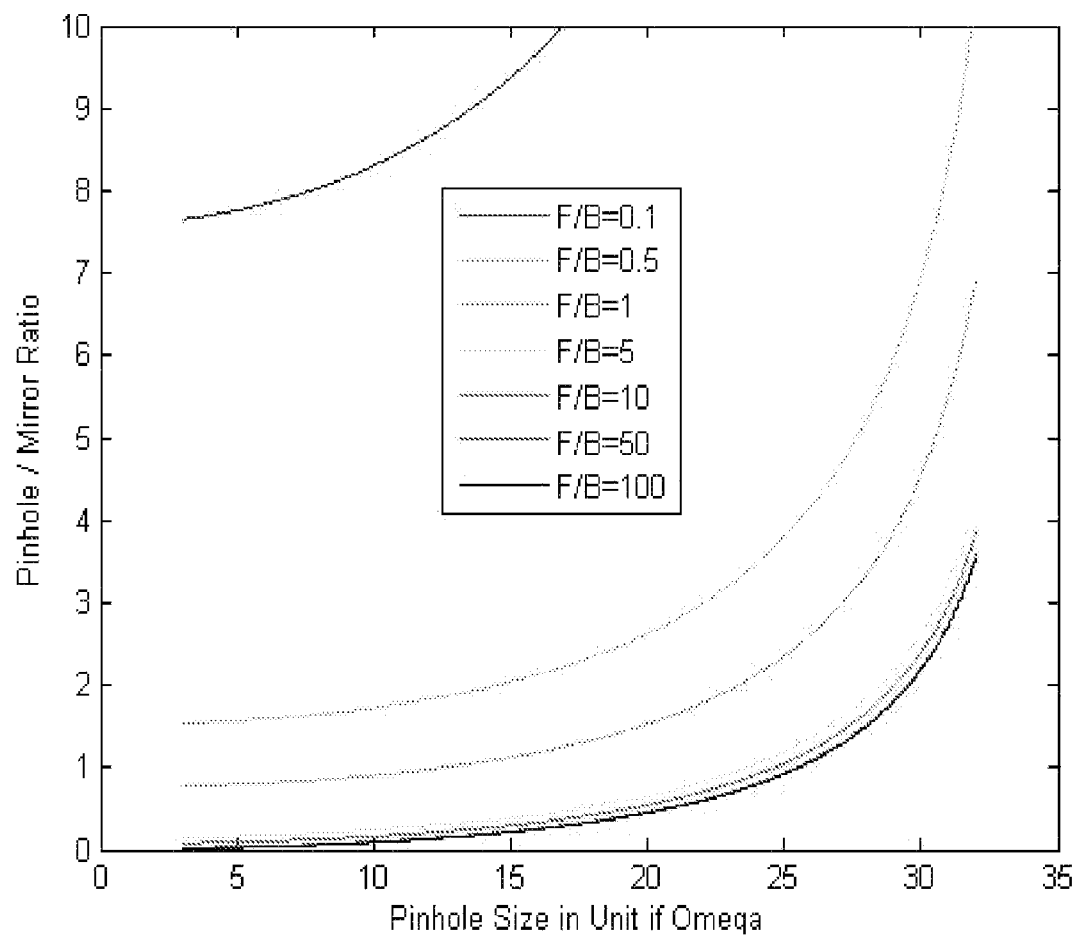
FIG. 2 graphically shows P/M ratio vs. pinhole size curves at different collagen SHG F/B ratios, based upon Eq. (4) herein below, according to an illustrative aspect of the invention.

Here, T % and R % represent the transmission and reflection coefficients of the pinhole and the mirror respectively, $\alpha$ represents the relative efficiencies of the detection pathways and the PMTs downstream of the pinhole mirror, while P and M represent the detected signal in PMT-1 and -2, respectively. Since T % and R % are constants, their ratio can be represented by another constant A. Plots of the pinhole vs. mirror-detected SHG ratio (P/M) as a function of the pinhole size are shown in FIG. 2, where we assumed R=12.7 mm, $\omega$=350 µm, A~1, and C=0.0005. In FIG. 2, the curve values are as follows:
  (a): F/B=0.1
  (b): F/B=0.5
  (c): F/B=1.0
  (d): F/B=5.0
  (e): F/B=10
  (f): F/B=50
  (g): F/B=100.

From these plots in FIG. 2, it can be seen that for collagen fibers with different SHG F/B ratios, the shape of the P/M ratio vs. pinhole size curves are different. Since the actual size of the pinhole is known, the real SHG F/B ratio can be determined by experimentally measuring the ratio of the SHG intensities collected by the two different PMTs, and eliminating unknown constants by a calibration step. It can further be seen that when the SHG F/B ratio is larger than ~5, the P/M ratio vs. pinhole size curves are too close to each other to distinguish given typical experimental noise. This suggests that it may be particularly advantageous to determine the F/B ratio for samples with SHG F/B ratios less than ~5.

A convenient simplification arises if we consider the terms in brackets in equation (4). When the SHG F/B ratio is smaller than 5 and n=3, $$\frac{B}{F} \cdot \frac{1}{2C}(1-\exp(-2n^2))$$

is much larger than $n^2$ for typical values of C. By neglecting the $n^2$ term, i.e., the forward-propagating and subsequently backscattered SHG that gets through the pinhole, the P/M ratio is inversely proportional to the SHG F/B ratio:

$$\frac{P}{M} = \frac{B}{F} \cdot \left[\frac{A\alpha}{C} \cdot \frac{(1-\exp(-2n^2))\omega^2}{2(R^2 - n^2\omega^2)}\right]. \quad (5)$$

This simplification streamlined data analysis while producing less than 10% systematic error in the worst case (i.e., when F/B=5).

The embodied method was applied to a rat tail tendon, since it is a sample whose SHG properties have been well studied. A whole rat tail was removed from a previously sacrificed animal. To generate a clear SHG image of the tendon, we peeled a thin layer of outer skin off the rat tail at the location of interest and exposed the tendon beneath it. We then put the rat tail on a glass slide with the exposed collagen fiber facing up, and we put another coverslip on top of the collagen fibers to assist in maintaining a meniscus for our water immersion objective. The rat tail and coverslip were then fixed on the glass slide with plastic tape and the collagen fibers were imaged though the coverslip.

Figure 3:
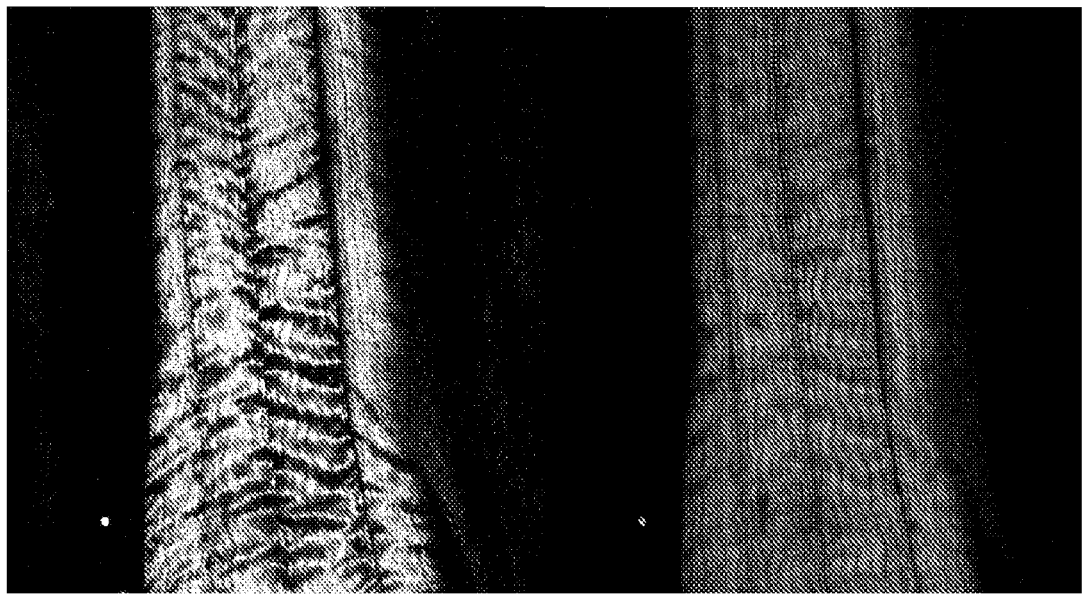
FIG. 3 shows (a) pinhole and (b) minor images of rat tail tendon collagen fibers according to an illustrative aspect of the invention. (Images are 600 um across).

We prepared whole rat tail samples from four separate animals. On each rat tail we chose five image fields. For each image field we generated two SHG images simultaneously. One SHG image was generated by PMT-1 (FIG. 1), which detected SHG signal that passed through the pinhole. The other SHG image was generated by PMT-2 (FIG. 1), which detected SHG signal that was reflected by the pinhole minor. For each rat tail, we also generated one image with no sample in order to quantify the background noise. One example of these image pairs is shown in FIG. 3. The bright spot 301 in the image is a fluorescent bead that we used for calibration, according to an exemplary aspect as follows.

In this exemplary aspect in which a fluorescent bead was used for calibration, the quantities in the square brackets in Eq. (5) must be determined in order to determine F/B. While α, A, n, R, and ω are dependent upon the instrument and are not expected to vary considerably, the C factor is a function of object (e.g., tissue) scattering and absorption underneath the image plane and may vary considerably from sample to sample. To address this concern, we applied a dilute solution of 10 μm diameter blue fluorescent polystyrene beads (10m365415, Invitrogen) to the surface of the sample. Since the unknown constants are the same for both collagen and the beads, the P/M ratio is inversely proportional to the SHG F/B ratio:

$$\frac{\left(\frac{P}{M}\right)_{collagen}}{\left(\frac{P}{M}\right)_{beads}} = \frac{(F/B)_{beads}}{(F/B)_{collagen}}. \quad (6)$$

The P/M ratio of beads and collagen can be calculated from pinhole and mirror images, and the true F/B ratio of beads can also be conveniently measured separately, which allows the calculation of the true F/B ratio of collagen fibers with Eq. (6).

To quantify the P/M ratio from pinhole and minor images, the background signal was first subtracted from the individual pinhole and mirror images, then the P/M ratio of all pixels was calculated. In regions of the original pinhole or mirror images where there was no significant collagen SHG or bead TPEF, the P/M ratio fluctuates due to small variations in background noise around a pixel count of zero, and lacks physical meaning. Consequently, an intensity threshold was chosen based upon the pinhole image, producing a binary image mask, which set the background pixels to zero and the foreground (e.g. collagen) pixels to one. This mask was multiplied by the P/M ratio image, setting the varying background pixels to zero. Image J analysis software was then used to calculate the average pixel count of the resultant masked P/M image, and this was divided by the average pixel count of the binary mask image, producing the average P/M ratio of all pixels within fibrils or beads (i.e., all pixels above threshold in the original pinhole image). The P/M ratio was calculated for both beads and collagen separately and then the collagen SHG F/B ratio was determined by equation (6) using the known bead F/B ratio.

As described above, we measured rat tail collagen SHG F/B ratios in four tails. For each tail we picked 5 ROIs and for each ROI we generated one pinhole image and one mirror image simultaneously. We then calculated P/M ratio for both the beads and the collagen and determined the average collagen SHG F/B ratio in that ROI from equation (6). The collagen SHG F/B ratio value for each of the four tails is then an average of the average SHG F/B ratio in five ROIs. The results are listed in the Table 1, where for each animal, means±standard deviations are presented from five ROIs. The average value for the four animals is then presented ±the standard deviation.

TABLE 1

|  | Animal I | Animal II | Animal III | Animal IV | Average |
|---|---|---|---|---|---|
| F/B ratio | 1.66 ± 0.17 | 0.98 ± 0.27 | 1.65 ± 0.34 | 1.14 ± 0.43 | 1.36 ± 0.35 |

To verify the validity of the method, we compared the results to traditional, directly measured rat tail collagen SHG F/B ratio. In the traditional direct measurement, we used both a forward and a backward detector, and the sample was sectioned in ~10 μm thin slices. This measurement was performed previously on five tails, producing an average value of 1.76±0.45 (mean±standard deviation). To compare the results from the instant method to that from the traditional direct measurement, we performed the Kolmogorov-Smirnov test, producing a p-value of 0.2857143, indicating that these two sets of data are not significantly different from each other. This suggests that the new method produces an accurate measurement of F/B using a single epi-detection objective lens, and does so from a single image scan.

Advantageously, the F/B ratio in many biological samples is at or below five, including the rat tail tendon (F/B ~1), skeletal muscle fascia (F/B ~5), cellulose (F/B ~4), ovarian cancer (F/B ~3.4), and dermis with (F/B ~3.4) and without (F/B~2.64) Osteogenesis Imperfecta. Thus the embodied technique may be applied as a noninvasive diagnostic tool for these two types of diseases.

The disclosed embodiments of the invention assumed no subsequent scattering of the direct back-propagating SHG signal, therefore it was limited to surface, or extremely shallow, imaging depths, making it suitable for quantifying F/B ratios 'on' intact thick tissue samples, but not necessarily 'in' intact thick tissue samples.

As embodied, the invention enables a faster imaging process as well as being extremely tolerant to sample movement during the imaging process. This allows F/B ratio measurements to be done in a dynamic fashion, and offers the realization of endoscopic measurements.

Ongoing work pertaining to the embodiments of the invention are directed to apparatus and method for rapidly assessing/evaluating tumor margins in an intact (i.e., unsliced) tissue section such as that typically removed during breast conservation surgery. This development includes optimizing the embodied method disclosed herein above for e.g., excised breast tumor tissue, which includes shifting the range of F/B ratios, optimizing the calibration step for determining C, and optimizing the scan rate parameters. After optimization, we will determine what tumor types the method can distinguish, the depth through healthy tissue that we can probe, and the minimum size of tumor cell clusters that we can distinguish.

More specifically, the aims include:

1) Shifting the range of F/B values to which the method is sensitive. The instant method is optimized to perform best with the extremely well characterized rat tail tendon, which is the subject of study of a large number of SHG papers. This form of collagen has a relatively low F/B ratio (~1), which means that the offset in equation 1 is low relative to the central peak, and the primary optical challenge is to ensure that a sufficient amount of the offset signal is detected. DCIS and healthy breast tissue from patients has a relatively high F/B ratio (~60; FIG. 5, also seen in our previous murine breast tumor model studies). Consequently, the primary optical challenge is to reduce the amount of the offset relative to the Gaussian central peak within the pinhole. This will serve to shift the window of sensitivity of our technique from low to high F/B ratios. To accomplish this we will exploit one or more of three complementary techniques:

a) Angular Selection.

The forward-propagating, multiply scattered SHG light that reaches the object plane via photon diffusion is distributed uniformly in space, and passes through the object plane at random angles. Conversely, the backward-propagating SHG light is contained in a relatively narrow "beam" of small angles around the laser axis. Re-imaging the back of the pinhole mirror with a second lens, and placing a simple pinhole in the Fourier plane will pass light that passes through the pinhole minor at a narrow "beam" of small angles while attenuate light that passes through the pinhole minor at wider angles.

b) Polarization Selection.

The forward-propagating, multiply scattered SHG light that reaches the object plane via photon diffusion is randomly polarized. Conversely, the polarization of the backward-propagating SHG light is closely coupled to the polarization of the excitation beam. Implementing a polarization selection step in back of the pinhole mirror will consequently attenuate the offset relative to the central peak.

c) Coherence Selection.

The forward-propagating, multiply scattered SHG light that reaches the object plane via photon diffusion has a random phase. Conversely, the backward-propagating SHG light is coherent and can be selected relative to incoherent light with a reference arm. This is the basis of second harmonic optical coherence tomography. Consequently, adding a reference arm in back of the pinhole minor will attenuate the offset relative to the central peak.

2) Evaluating alternate calibration strategies to determine which one is ideal for a particular application. The disclosed calibration method of using a dilute solution of blue beads adds an additional sample handling step that is non-ideal. Alternative approaches include.

a) Tissue Autofluorescence.

We will evaluate the reproducibility of the F/B ratio and C parameter of NADH autofluorescence in samples from diverse breast tissue and breast tumor types, and determine if there is a predictable relationship between this ubiquitous intrinsic fluorophore's C parameter (at 420-460 nm emission) and the C parameter of SHG (at 405 nm).

b) A Blue Reference Laser.

We will evaluate the use of an appropriately aligned ~400 nm blue reference laser, directed into the sample collinearly with the SHG excitation laser, to provide a measure of C based upon its diffuse backscattered light.

c) A Lookup Table.

Using our established solution of blue beads as a reference source with known F/B, we will quantify the variability in C values for different tissue and tumor types.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed. No language in the specification should be construed as indicating any non-claimed element as essential to the practice of the invention.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. A medical diagnostic system enabling the detection of a second-harmonic-generation-forward/backward (SHG F/B) ratio from a subject, comprising:
   a beam scanning component;
   a subject plane imaging component optically coupled to the beam scanning component, wherein the subject plane imaging component is an epi-imaging system;
   an imaging component disposed in an optical path of the system to provide a conjugate image of the subject plane in an image plane;
   an image discriminating component disposed in the image plane;
   a first detector disposed in a first optical path from the image discriminating component to detect at least one of the direct backward-propagating SHG and the backscattered forward-propagating SHG;
   a second detector disposed in a second optical path from the image discriminating component to detect at least one of the other respective backscattered forward-propagating SHG and the direct backward-propagating SHG; and a processor to calculate the second-harmonicgeneration-forward/backward ratio, from the data received by the two detectors.

2. The optical system of claim 1, wherein the subject imaging component is a microscope.

3. The optical system of claim 1, wherein the imaging component is one or more imaging lens elements.

4. The optical system of claim 1, wherein the image discriminating component is a pinhole minor.

5. The optical system of claim 4, wherein the first detector is disposed adjacent one side of the pinhole mirror and the second detector is disposed adjacent an opposite side of the pinhole minor.

6. The optical system of claim 4, wherein the pinhole minor has a central clear aperture and a reflective surface outside of the central clear aperture.

7. The optical system of claim 6, wherein the central clear aperture has an anti-reflection coating.

8. The optical system of claim 4, wherein the pinhole mirror has a central clear aperture having a radius equal to or greater than about 10 microns.

9. The optical system of claim 1, further comprising a spectral filter disposed in front of the first detector.

10. The optical system of claim 9, further comprising a spectral filter disposed in front of the second detector.

11. A medical diagnostic method for measuring a second-harmonic-generation-forward/backward (SHG F/B) ratio from a subject, comprising the steps of:
    irradiating a subject in a manner to generate a second harmonic generation (SHG) emission in a subject plane from the subject including a direct backward-propagating SGH portion and a backscattered forward-propagating SHG portion of the SHG emission;
    imaging the direct backward-propagating SHG and the backscattered forward-propagating SHG via epi-imaging onto a single confocal image plane;
    providing an image discriminating component in the confocal image plane that transmits either the confocal imaged direct backward-propagating SHG or the confocal imaged backscattered forward-propagating SHG and reflects either the respective confocal imaged backscattered forward-propagating SHG or the confocal imaged direct backward-propagating SHG;
    detecting the transmitted SHG emission with a first detector and the reflected SHG emission with a second detector and measuring SHG F/B ratio using data from the first and second detector.

12. The method of claim 11, comprising transmitting the confocal imaged direct backward-propagating SHG or the confocal imaged backscattered forward-propagating SHG through a clear aperture in the confocal image plane to the first detector and reflecting the respective confocal imaged backscattered forward-propagating SHG or the confocal imaged direct backward-propagating SHG from the confocal image plane to the second detector.

13. The method of claim 12, further comprising disposing a pinhole minor having the clear aperture and a reflective surface in the confocal image plane, wherein the clear aperture has a radius equal to or greater than 10 microns.

14. The method of claim 12, further comprising disposing a pinhole minor having the clear aperture and a reflective surface in the confocal image plane, wherein the clear aperture has a radius equal to or greater than 30 microns or substantially equal to or greater than approximately $3\omega$, wherein the total SHG emission distribution on the subject plane is expressed as $$I_{SHG}(r) = B\exp\left[-2\left(\frac{r}{\omega}\right)^2\right] + FC,$$

where $\omega$ is the $e^{-2}$ Gaussian spot size of the direct backward propagating SHG, F and B are absolute intensities of forward and backward propagating SHG signals, C relates the initial forward propagating signal intensity to the average intensity of the uniform distribution of SHG light that reaches the object plane and is a function of scattering and absorption properties of the underlying tissue, and has a value between $10^{-4}$ and $10^{-3}$.

* * * * *